(12) United States Patent
Bystrzynski et al.

(10) Patent No.: US 9,884,135 B2
(45) Date of Patent: Feb. 6, 2018

(54) SMART OPTIC CONTROLLER FOR A HYDROXYL GENERATOR UNIT

(71) Applicant: HGI Industries, Inc., Boynton Beach, FL (US)

(72) Inventors: Richard Mariusz Bystrzynski, Merrylands (AU); Richard Anthony Zessin, Bensville (AU); Adrian Philip Lake, Ourimbah (AU); Stephen John Sommer, Berowra Heights (AU)

(73) Assignee: HGI Industries, Inc., Boynton Beach, FL (US)

(*) Notice: Subject to any disclaimer, the term of this patent is extended or adjusted under 35 U.S.C. 154(b) by 0 days.

(21) Appl. No.: 15/358,952

(22) Filed: Nov. 22, 2016

(65) Prior Publication Data

US 2017/0143867 A1    May 25, 2017

Related U.S. Application Data

(60) Provisional application No. 62/259,151, filed on Nov. 24, 2015.

(51) Int. Cl.
*A61L 9/20* (2006.01)
*A61L 9/015* (2006.01)

(52) U.S. Cl.
CPC ............ *A61L 9/20* (2013.01); *A61L 2209/111* (2013.01)

(58) Field of Classification Search
USPC ...... 250/504 R, 526; 422/1, 4, 5, 20, 21, 24, 422/186.07, 186.3
See application file for complete search history.

(56) References Cited

U.S. PATENT DOCUMENTS 9,168,323 B2    10/2015  Morneault
2006/0034737 A1*  2/2006  Beam .................... A61L 9/205
                                                        422/186.07
(Continued)

FOREIGN PATENT DOCUMENTS

CA    2178432    12/1996

OTHER PUBLICATIONS

International Search Report dated Mar. 3, 2017 for PCT application PCT/US/63452.

*Primary Examiner* — Bernard Souw
(74) *Attorney, Agent, or Firm* — Fleit Gibbons Gutman Bongini Bianco PL; Jon A. Gibbons

(57) ABSTRACT

A hydroxyl generator unit includes an ultraviolet light source, a reaction chamber within interior space of the hydroxyl generator unit, environmental sensors and a smart optic controller coupled to environmental sensors and to the ultraviolet light source. The smart optic controller integrates environmental conditions, and in response to at least the environmental conditions, the smart optic controller generates an output signal to the ultraviolet light source to control to the hydroxyls generated by the hydroxyl generator unit. The smart optic controller includes at least one of an air flow sensor, a temperature sensor, a humidity sensor and a light sensor, to control operation of the hydroxyl generator unit. The smart optic controller includes a microcontroller that interrogates the sensors and that interfaces to external systems. The smart optic controller includes a near field communications circuit attached to a sensor communications link, and a control interface via an RS-485 connection.

7 Claims, 19 Drawing Sheets

(56) References Cited

U.S. PATENT DOCUMENTS

2006/0104858 A1* 5/2006 Potember ............... A61L 9/015
 422/4
2007/0119699 A1 5/2007 Chambers et al.
2014/0364972 A1 12/2014 Minvielle

* cited by examiner

Table 1: Comparison of Various Oxidizing Potentials

| Oxidizing Agent | Electrochemical Oxidation Potential, (EOP)V | EOP Relative to Chlorine |
|---|---|---|
| Fluorine | 3.06 | 2.25 |
| Hydroxyl Radical | 2.80 | 2.05 |
| Oxygen (Atomic) | 2.42 | 1.78 |
| Ozone | 2.08 | 1.52 |
| Hydrogen Peroxide | 1.78 | 1.30 |
| Hypochlorite | 1.49 | 1.10 |
| Chlorine | 1.36 | 1.00 |
| Chlorine Dioxide | 1.27 | 0.93 |
| Oxygen (Molecular) | 1.23 | 0.90 |

Sources:

www-rcf.usc.edu/~pirbazar/group_homepage/resear/adv.html
www.iupac.org/publications/pac/1998/pdf/7012x2271.pdf

FIG. 1

Rear

Front

| Test Organism | Carrier Type | Exposure Time | Percent Reduction | Log10 Reduction | Organism Significance |
|---|---|---|---|---|---|
| Aspergillus niger (ATCC 16404) | Stainless Steel | 48 hrs | >99.9% | 3.5 | Aspergillus niger is considered one of the most resilient fungal strains and is identified by the EPA as a "reference organism" for testing purposes pertaining to the Mold group. |
| | | 72 hrs | >99.99% | 4.4 | |
| | | 96 hrs | >99.99% | >4.4 | |
| | Cotton Fabric | 48 hrs | 97.00% | 1.52 | |
| | | 72 hrs | 98.50% | 1.81 | |
| | | 96 hrs | 99.60% | 2.37 | |
| Staphylococcus aureus (ATCC 6538) | Stainless Steel | 4 hrs | 93.90% | 1.21 | Antimicrobial efficacy against Staphylococcus aureus is frequently required by the US EPA and is identified as a "reference bacterium" for Gram positive bacterium for testing purposes. |
| | | 8 hrs | >99.8% | 2.84 | |
| | | 12 hrs | >99.999% | >5.1 | |
| | Cotton Fabric | 4 hrs | >99.9% | >3.5 | |
| | | 8 hrs | >99.9% | >3.5 | |
| | | 12 hrs | >99.9% | >3.5 | |
| Escherichia coli (ATCC 11229) | Stainless Steel | 4 hrs | >99.99% | >4.2 | In the food processing sector, another important representative pathogen is the Gram negative bacterium Escherichia coli. |
| | | 8 hrs | >99.99% | >4.2 | |
| | | 12 hrs | >99.99% | >4.2 | |
| | Cotton Fabric | 4 hrs | >99.9% | >3.4 | |
| | | 8 hrs | >99.9% | >3.4 | |
| | | 12 hrs | >99.9% | >3.4 | |

  

FIG. 21

| | | | | |
|---|---|---|---|---|
| Pseudomonas aeruginosa (ATCC 15442) | Stainless Steel | 4 hrs | >99.999% | >5.1 |
| | | 8 hrs | >99.999% | >5.1 |
| | | 12 hrs | >99.999% | >5.1 |
| | Cotton Fabric | 4 hrs | >99.9% | >3.5 |
| | | 8 hrs | >99.9% | >3.5 |
| | | 12 hrs | >99.9% | >3.5 |
| Salmonella enterica serotype typhimurium (ATCC 23564) | Stainless Steel | 1 hr | 36.90% | 0.20 |
| | | 3 hrs | 88.50% | 0.94 |
| | | 5 hrs | 94.20% | 1.24 |
| | | 8 hrs | >99.99% | >4.41 |
| | Cotton Fabric | 1 hr | 78.60% | 0.67 |
| | | 3 hrs | 92.80% | 1.14 |
| | | 5 hrs | 96.00% | 1.40 |
| | | 8 hrs | >99.999% | >5.87 |

Pseudomonas aeruginosa is frequently required by the US EPA as a representative pathogen of clinical importance. This bacterium is often associated with hospital-acquired infections. Pseudomonas aeruginosa is a "reference bacterium" for Gram negative bacterium testing purposes.

Gram-negative rod-shaped bacteria. This is one of the most common causes of food poisoning in the United States. An estimated 1.2 million cases occur annually; of these, approximately 42,000 are laboratory-confirmed cases reported to CDC. There are currently 2,463 serotypes of Salmonella.

FIG. 21 CONTINUED

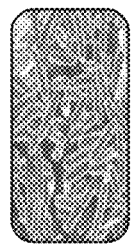

| Test Organism | Carrier Type | Exposure Time | Percent Reduction | Log10 Reduction | Organism Significance |
|---|---|---|---|---|---|
| CRE – Klebsiella pneumoniae (CDC 1000527) | Stainless Steel | 4 hrs | 67.60% | 0.49 | Gram-negative bacteria that can cause different types of healthcare-associated infections, including pneumonia, bloodstream infections, wound or surgical site infections, and meningitis. Increasingly, Klebsiella bacteria have developed resistance, most recently to the class of antibiotics known as carbapenems. |
| | Stainless Steel | 8 hrs | 69.70% | 0.52 | |
| | Stainless Steel | 12 hrs | 89.80% | 0.99 | |
| | Cotton Fabric | 4 hrs | 99.40% | 2.21 | |
| | Cotton Fabric | 8 hrs | >99.9% | >3.46 | |
| | Cotton Fabric | 12 hrs | >99.99% | >4.19 | |
| Influenza A virus (ATCC VR-544) | Glass | 3 hrs | 99.98% | 3.7 | Representative Organism Influenza type A viruses are the most dangerous human pathogens among the influenza types and cause the most severe disease. Influenza epidemics result in 250,000 to 500,000 deaths globally each year. |
| | Glass | 6 hrs | ≥99.997% | ≥4.5 | |
| | Cotton Fabric | 3 hrs | 99.999% | 5.25 | |
| | Cotton Fabric | 6 hrs | ≥99.9997% | ≥5.5 | |
| Listeria monocytogenes (ATCC 19111) | Stainless Steel | 4 hrs | 94.7% | 1.27 | Listeria monocytogenes is a gram-positive, rod-shaped bacterium responsible for listeriosis, a lethal food-borne infection that has a devastating fatality rate of 25% (Salmonella, in comparison, has less than 1% mortality rate). It is incredibly hardy and able to grow in temperatures ranging from 39°F (4°C) to 99°F (37°C) |
| | Cotton Fabric | 4 hrs | 98.6% | 1.87 | |

FIG. 22

| | | | | |
|---|---|---|---|---|
| Clostridium difficile (ATCC 700792) | Stainless Steel | 48 hrs | >99.8% | >2.8 |
| | | 72 hrs | >99.8% | >2.8 |
| | | 96 hrs | >99.8% | >2.8 |
| | Cotton Fabric | 48 hrs | >98.2% | >1.7 |
| | | 72 hrs | >98.2% | >1.7 |
| | | 96 hrs | >98.2% | >1.7 | C. difficile is a spore-forming, gram-positive bacillus that causes potentially life-threatening colitis. Its spores can survive outside the human body for months on surfaces including bedrails, commodes, bedpans, thermometers, wheelchairs, endoscopes, bathing tubs, and the hands of health care workers. |
| PRRS Porcine Respiratory & Reproductive Syndrome virus (Strain NVSL) | Glass | 3 hr | 49.9% | 0.30 |
| | | 6 hrs | 97.90% | 1.68 | A small, enveloped RNA virus that causes a disease of pigs. This economically important pandemic causes reproductive failure in breeding stock and respiratory tract illness. The PRRS virus cost the US swine industry in excess of $560 million in losses each year. |

Antiviral and Antimicrobial efficacy of Odorox® Mobile Disinfection Unit (MDU™) Hydroxyl Generator

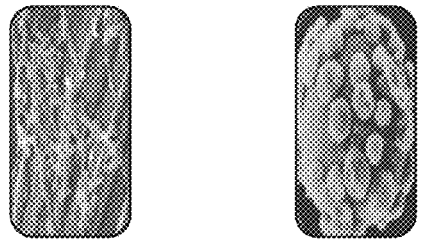

SMART OPTIC CONTROLLER FOR A HYDROXYL GENERATOR UNIT

CROSS-REFERENCE TO RELATED APPLICATION

This application is based upon and claims priority to Provisional Patent Application No. 62/259,151, filed Nov. 24, 2015, the entire disclosure of which is hereby incorporated by reference herein.

BACKGROUND

Field

The present invention relates to hydroxyl generators and in particular to a controller for a hydroxyl generator.

Related Art

Atmospheric hydroxyls (HO⁻ or OH) are naturally occurring free radicals in the troposphere. Hydroxyls are nature's way to make and keep air safe and breathable. Hydroxyls are created in earth's atmosphere when the sun's ultraviolet energy reacts with oxygen, ozone and water vapor. Hydroxyls are a lab-certified sterilant that is 100% safe for humans. Hydroxyls are the most potent and safe oxidizer. Hydroxyls remove odors on surfaces and odors, including pollution, cigarette smoke, and cooking and toilet smells, in air. Hydroxyls destroy volatile organic compounds (VOCs) and toxins including toxins contained in fine particulate matter having a diameter of 2.5 micrometers or less ($PM_{2.5}$). Hydroxyls kill bacteria, mold and viruses including those that cause influenza, staph, severe acute respiratory syndrome (SARS)—and helps prevent their spread. FIG. 1 is a comparison of known oxidizing potentials of various oxidizing agents.

BRIEF DESCRIPTION OF THE DRAWINGS

FIG. 1 is a comparison of known oxidizing potentials of various oxidizing agents.

FIGS. 21 and 22 show test results of a hydroxyl generator unit that includes the smart optic controller in accordance with one embodiment of the disclosure.

DETAILED DESCRIPTION

A hydroxyl generator unit 501 (see FIG. 5) in accordance with the disclosure incorporates a smart optic controller 202, coupled to an ultraviolet (UV) light source 504 (see FIG. 5) and a reaction chamber within interior space of the hydroxyl generator unit.

Figure 2:
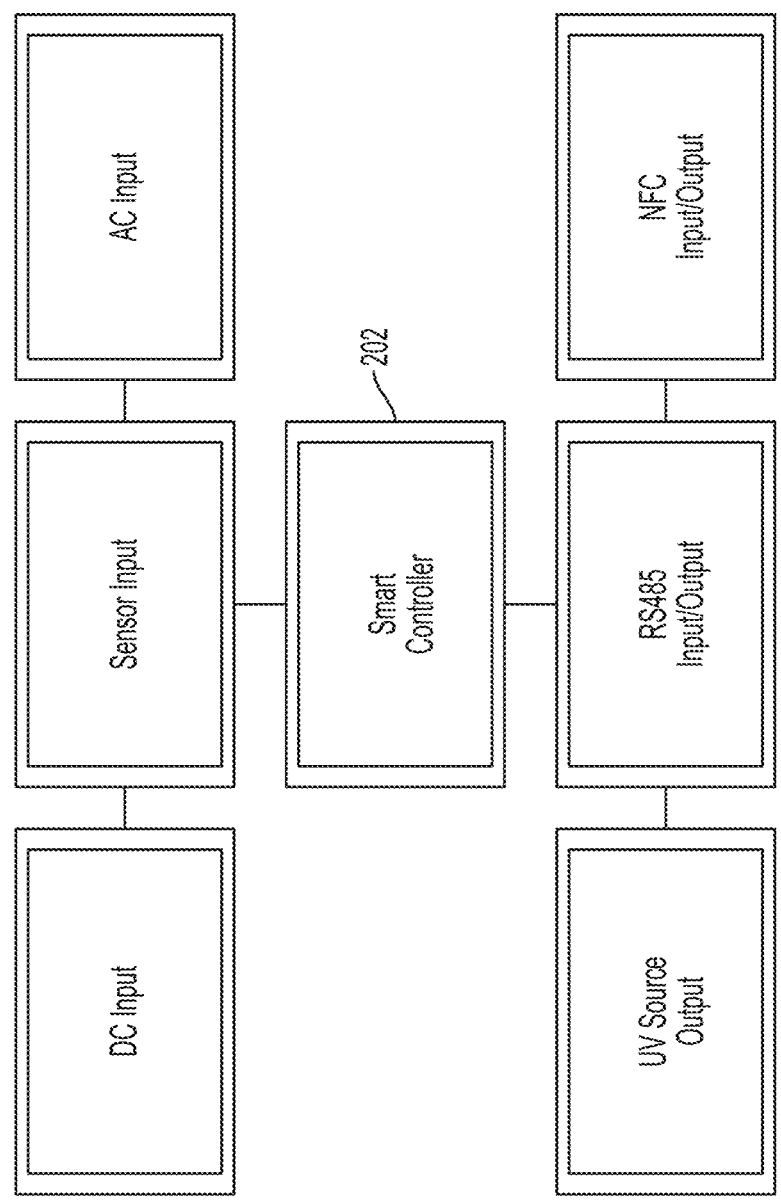
FIG. 2 is a simplified functional block diagram of a hydroxyl generator unit in accordance with one embodiment of the disclosure, including a smart optic controller in accordance with one embodiment of the disclosure.

FIG. 2 is a simplified functional block diagram of the hydroxyl generator unit 501 in accordance with one embodiment of the disclosure, including the smart optic controller 202 in accordance with one embodiment of the disclosure.

Figure 3:
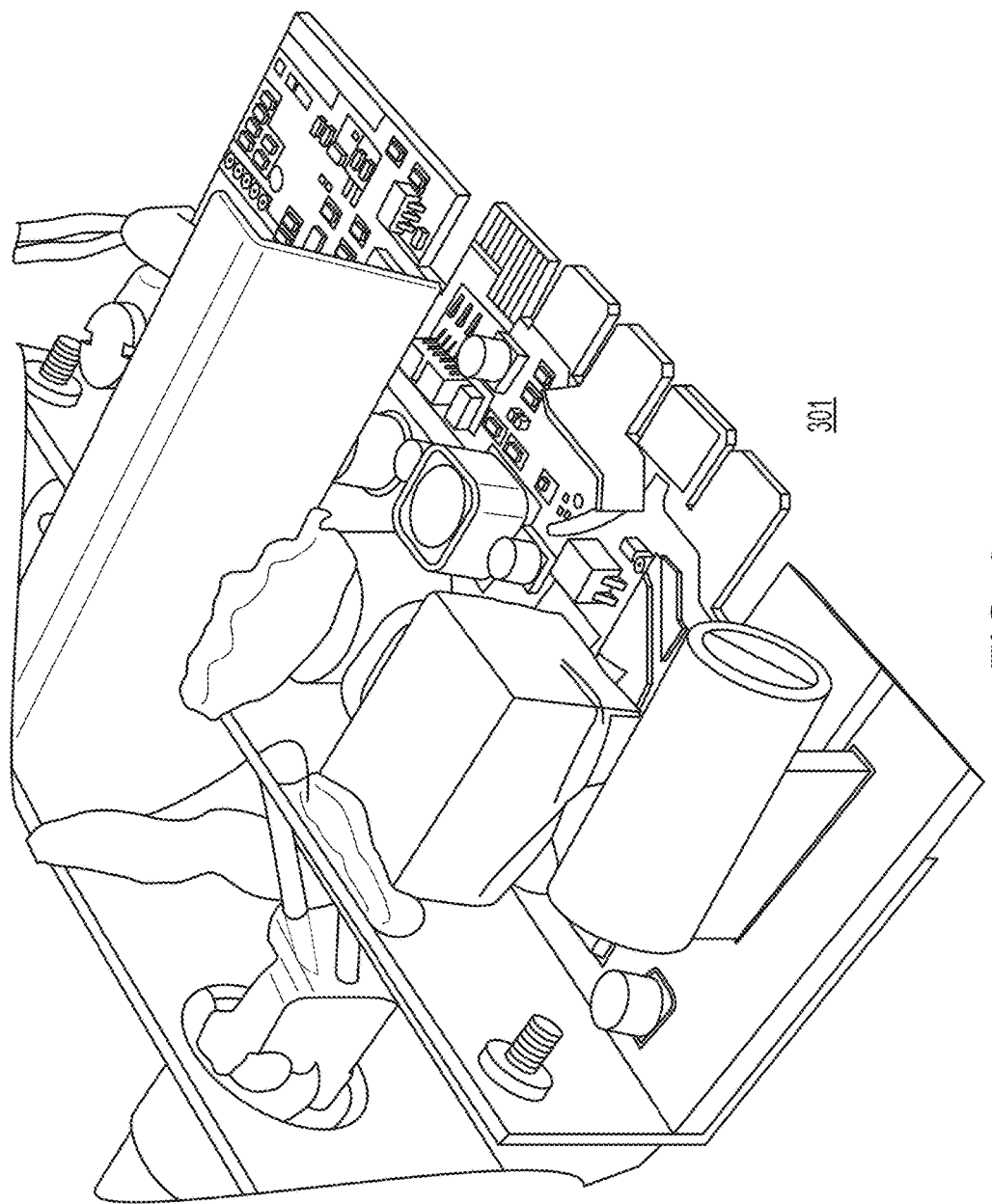
FIG. 3 is a photograph of a printed circuit board of the smart optic controller shown in FIG. 2.

FIG. 3 is a photograph of a printed circuit board 301 of the smart optic controller 202.

Figure 4:
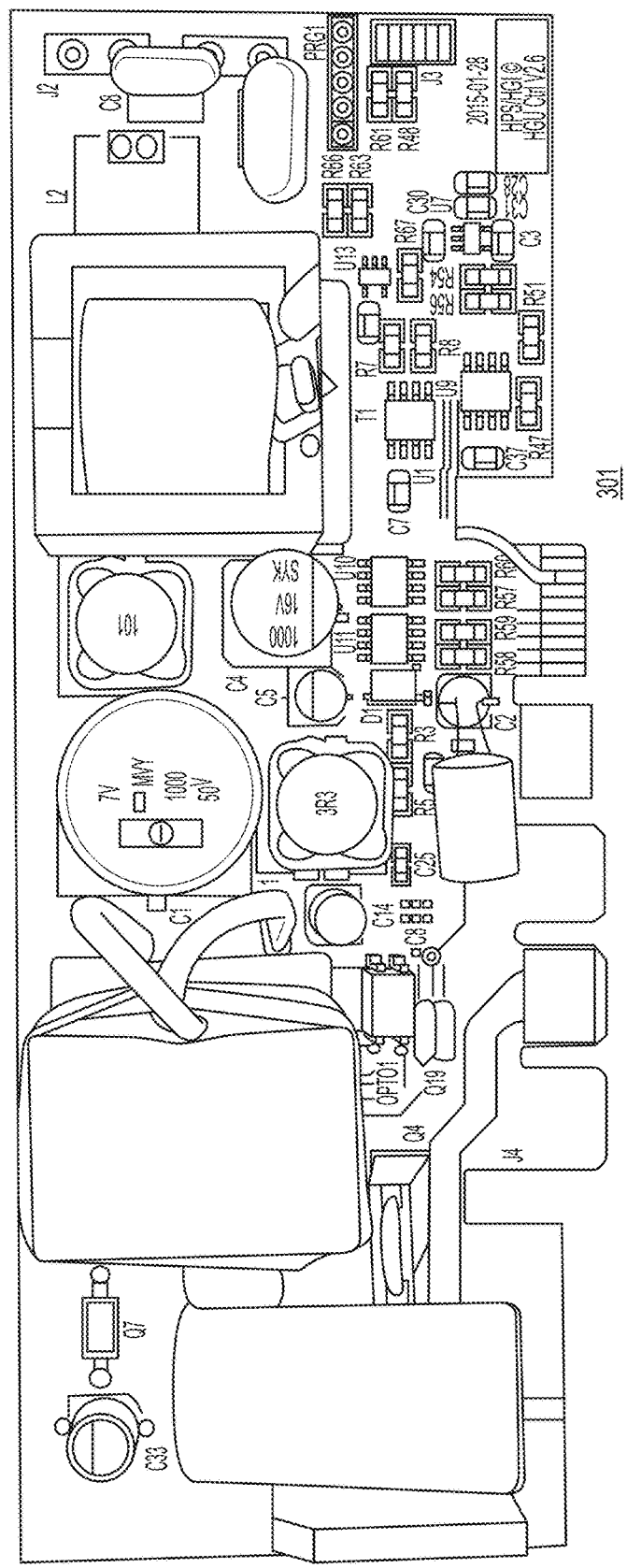
FIG. 4 is another photograph of the printed circuit board.

FIG. 4 is another photograph of the printed circuit board 301 of the smart optic controller 202.

The smart optic controller 202 integrates required functionality to power, control and monitor operation and environmental conditions to generate hydroxyls and to ensure that the hydroxyl generator unit is operating within defined operating conditions. The functionality implemented in the smart optic controller 202 depends on the application and may use any combination of its capabilities to ensure correct operation.

The smart optic controller 202 includes one or more of the following environmental sensors to control operation of the hydroxyl generator unit: an air flow sensor, a temperature sensor, a humidity sensor and a light sensor. The light sensor determines an output level of hydroxyls. The light sensor is also for cleaning detection. The air flow sensor provides information about the delivery of hydroxyls and can detect a clogged filter. Feedback from the environmental sensors helps the hydroxyl generator unit 501 maintain a fixed level of hydroxyls in the environment of the hydroxyl generator unit 501. In some embodiments, the smart optic controller 202 includes additional environmental sensors, such as a sensor that directly measures hydroxyls and a sensor that measures total oxidant levels.

The smart optic controller 202 includes a microcontroller (not shown) that drives and monitors a power system (not shown), interrogates the aforesaid environmental sensors and a fan power/fan control (if attached), and interfaces to external systems (for control, reporting or additional sensor information). The power system that can operate from a universal AC supply (90-280V AC @ 20-400 Hz) or DC input (12-30V DC). The power system generates fan power (6-18V DC), 3V3, and exports the DC input or 14V DC if powered by AC input.

Conditions of operation are: air flow is present, temperature is within range, humidity is within range, and light levels are zero before start (dark) and increase when the UV light source 504 is active.

Communications are active in the controller in two forms: 1) near field communications attached to a sensor communications link, and 2) a control interface via an RS-485 serial data communication port. User interfaces and other forms of communication are enabled via the RS-485 serial data communication port, which is flexible in the number of smart optic controllers 202 and control interfaces attached on the one connection. Using the RS-485 interface, wireless and other wired communications, such as ZigBee®, WiFi™, Bluetooth®, and Ethernet, and a RS-232 serial data communication port, are interfaced to the smart optic controller 202. The near field communications allows the reading of the status, log data and settings as well as changing the operating settings and configuring the smart optic controller 202.

The smart optic controller 202 integrates environmental information while controlling its output to a multi-wavelength UV light source 504 to generate hydroxyls. The smart optic controller 202 controls the intensity, i.e., amount, of hydroxyl produced by the hydroxyl generator unit 501.

The smart optic controller 202 is designed as a user-replaceable integrated device.

Figure 5:
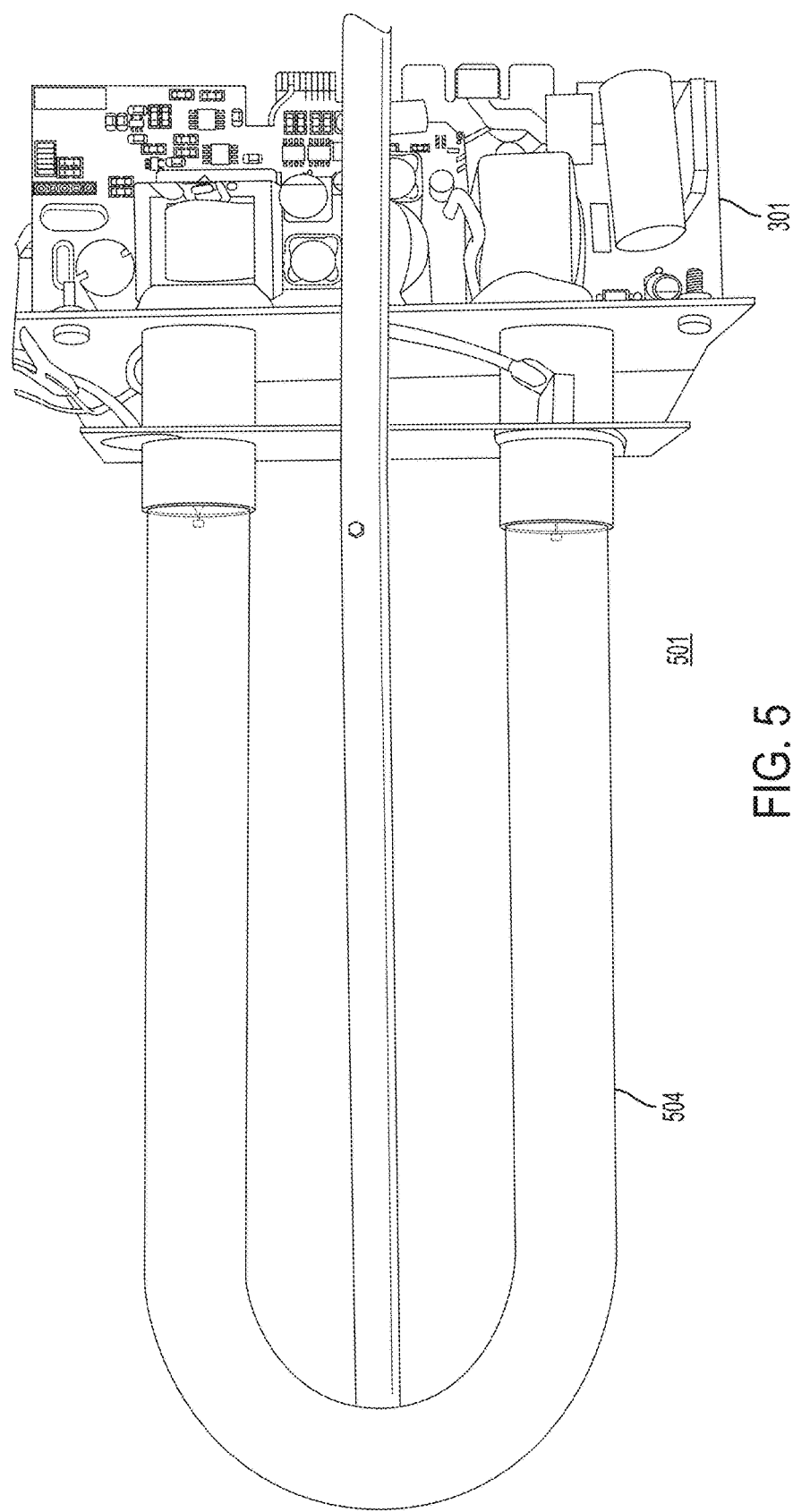
FIG. 5 is a photograph of a hydroxyl generator unit in accordance with one embodiment of the disclosure.

FIG. 5 is a photograph of a hydroxyl generator unit 501 in accordance with one embodiment of the disclosure. The hydroxyl generator unit 501 includes the smart optic controller 202 and a UV light source 504. In one embodiment, the hydroxyl generator unit 501 includes a single U-shaped optic in the reaction chamber. The single U-shaped optic acts as the UV light source 504.

Figure 6:
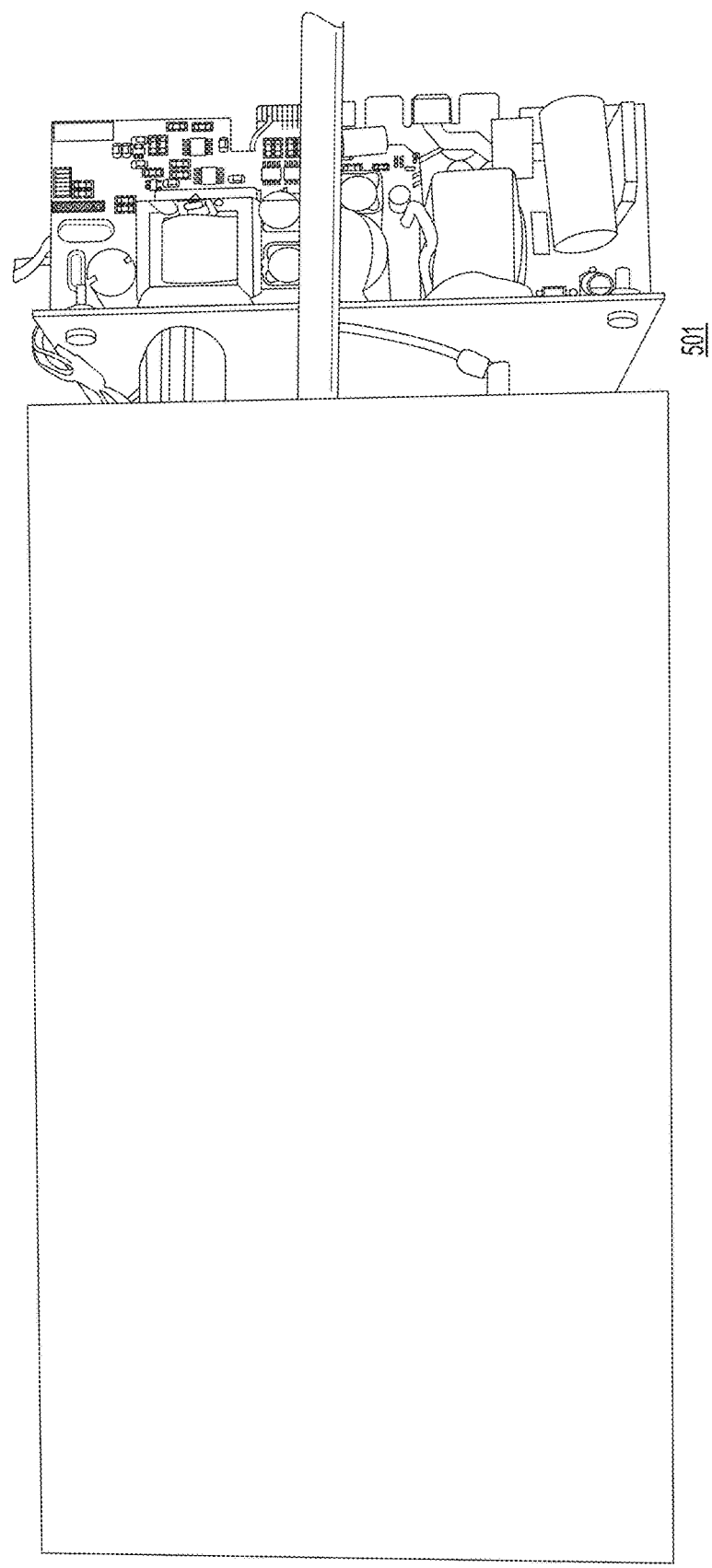
FIG. 6 is another photograph of the hydroxyl generator unit.

FIG. 6 is another photograph of the hydroxyl generator unit 501.

The hydroxyl generator unit (HGU) 501 recreates a natural process indoors to keep the air that you breathe safe and the space in which you live safe. The HGU 501 optimizes the reaction chamber, or interior space, airflow by increasing retention time, turbulence and introducing a more reflective material of the reaction chamber and inert material of the reaction chamber.

The HGU 501 is designed as a user serviceable component that incorporates the majority of possible failure points for a completed hydroxyl generation system. The HGU 501 includes an optimized reaction chamber to ensure complete reaction. The HGU 501 includes 90-280V AC and 12-30V DC operation. The HGU 501 includes a super-efficient fan and driver for low power and efficient operation. The HGU 501 includes an interlock for cover detection and remote interlock for safety.

The HGU 501 complies with industry standards for communications to control panel and integration to any industry standard control system/building management system.

The HGU 501 includes radio frequency identification (RFID) capabilities for debugging/tracking/inventory/copy protection—works powered on or off via mobile phone application. The HGU 501 includes a RFID tag coupled to the smart optic controller. The HGU 501 includes on-board monitoring of fan and tube operation. The HGU 501 includes a serial number embedded in a RF-IF and a microcontroller for copy protection and is integrated with a tube. The HGU 501 includes logging of run hours, starts, and fault history log/event with date and time. The HGU 501 includes a micro-controlled light level which is dimmable from about 20% to 100%. One embodiment of the HGU 501 includes a roof unit (not shown).

Figure 7:
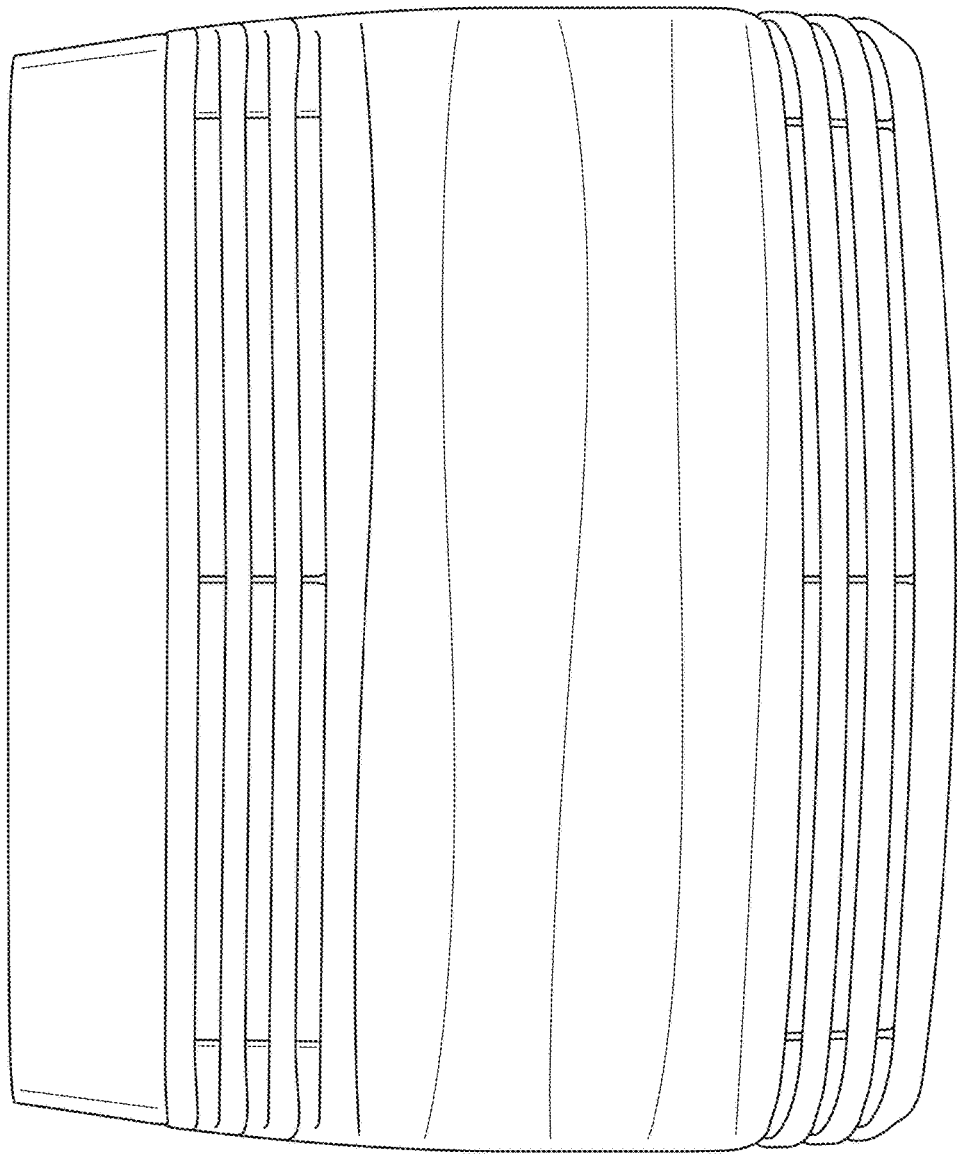
FIG. 7 is a front view of a personal unit in accordance with one embodiment of the disclosure.

FIG. 7 is a front view of a personal unit of the HGU 501 in accordance with one embodiment of the disclosure. The personal unit has a portable design.

Figure 8:
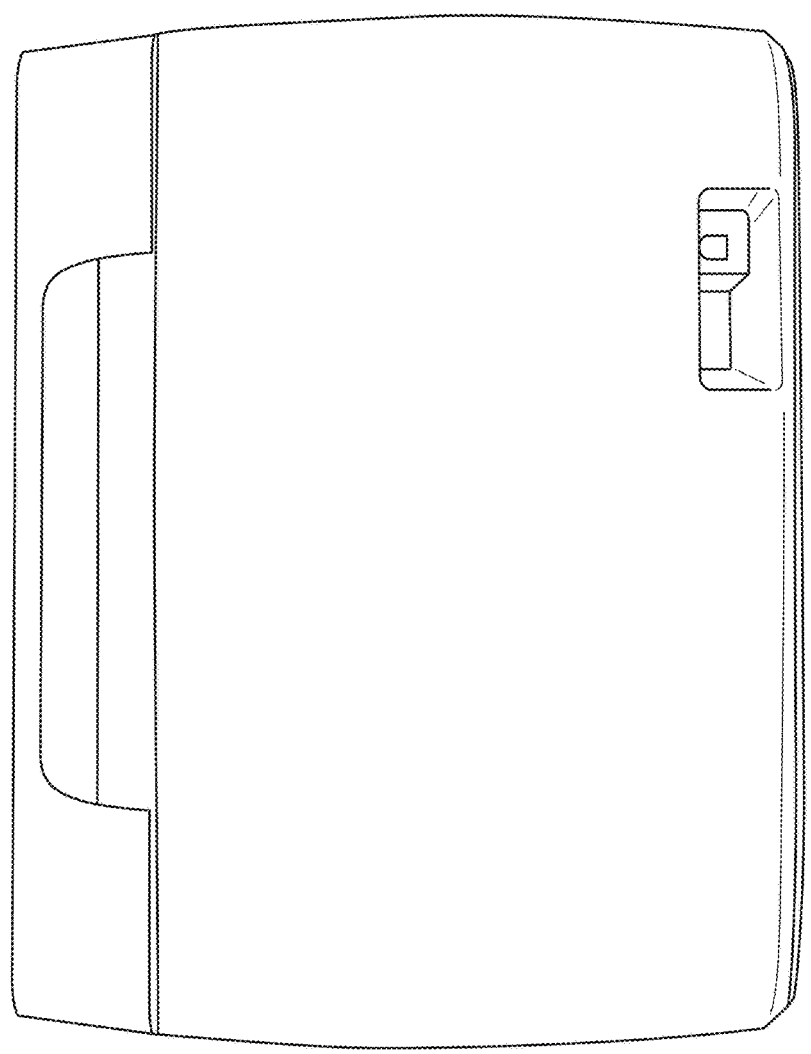
FIG. 8 is a back view of the personal unit.

FIG. 8 is a back view of the personal unit.

Figure 9:
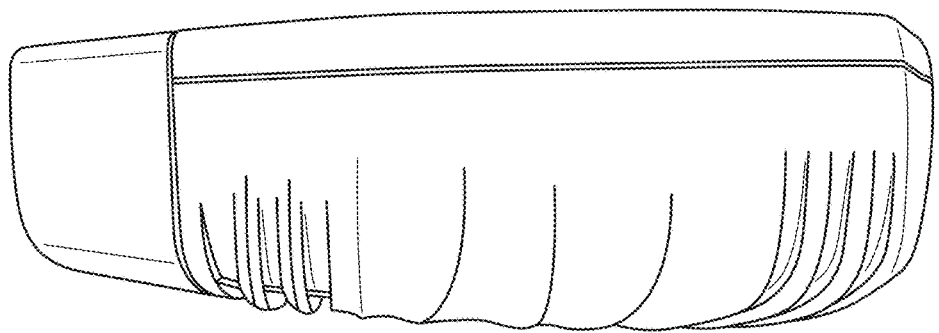
FIG. 9 is a side view of the personal unit.

FIG. 9 is a side view of the personal unit. The personal unit has a same capacity as the wall/roof unit. The personal unit includes a SmartUser interface with a near field communications (NFC) circuit, coupled to the smart optic controller 202, including provision for pairing and support. The personal unit includes a Bluetooth circuit, coupled to the smart optic controller 202, for controlling the personal unit from a tablet or a phone. The personal unit includes an organic light-emitting diode (OLED) display (not shown), coupled to the smart optic controller 202, and capacitive touch control screen (not shown).

Figure 10:
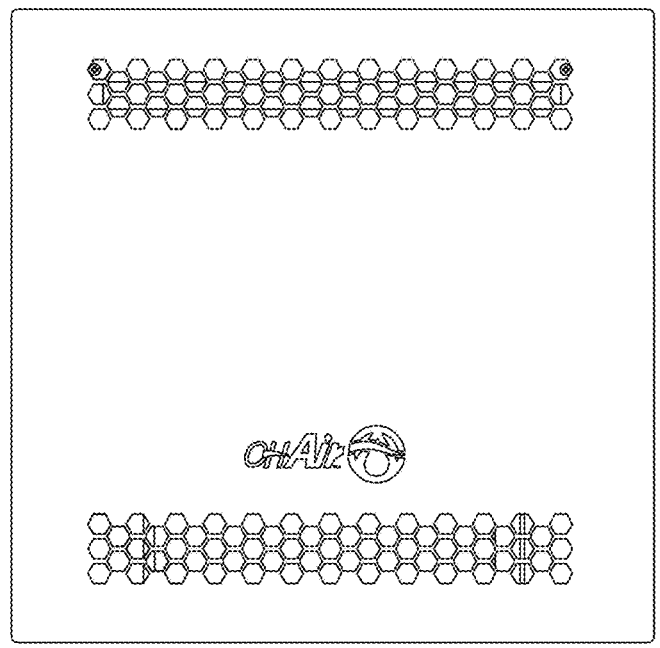
FIGS. 10, 11 and 12 are three views of an Architect™ unit in accordance with one embodiment of the disclosure.
Figure 11:
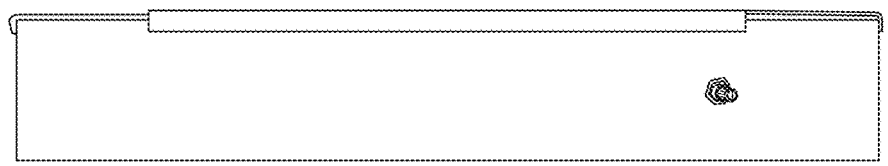
Figure 12:
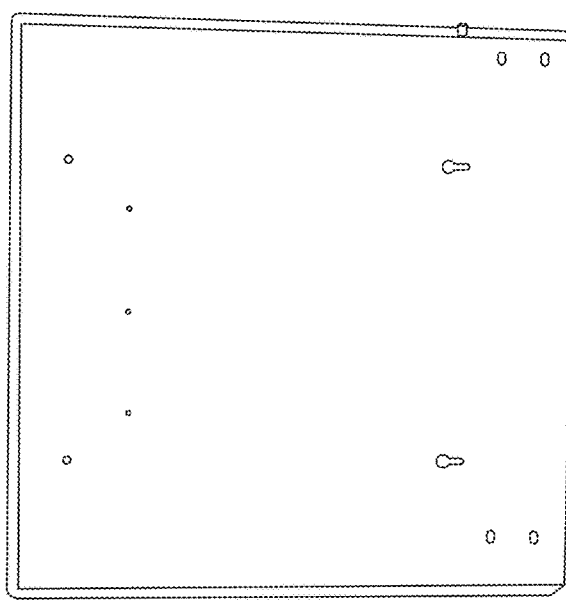

FIGS. 10, 11 and 12 are three views of an Architect™ unit in accordance with one embodiment of the disclosure.

Figure 13:
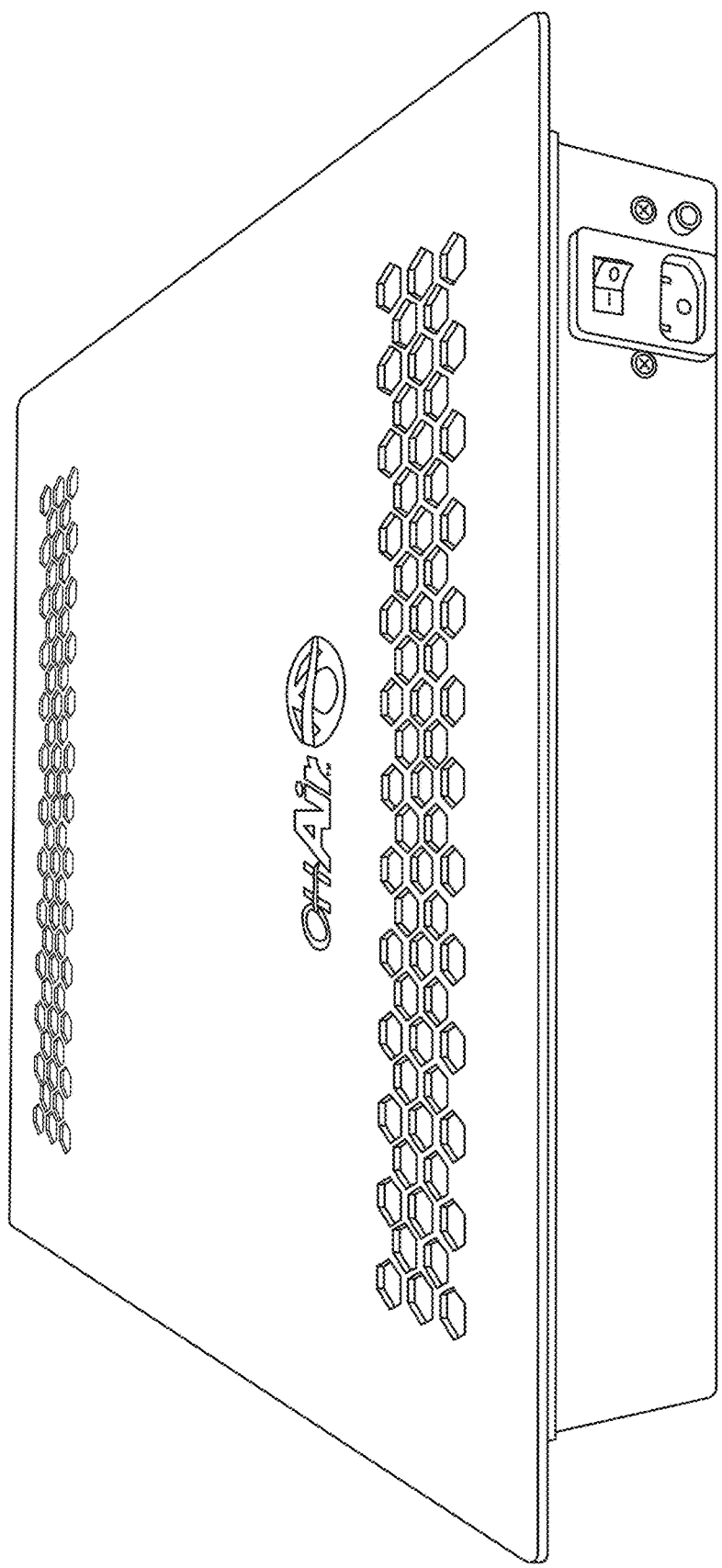
FIG. 13 is a photograph of a wall/flush-mount unit in accordance with one embodiment of the disclosure.

FIG. 13 is a photograph of a wall/flush-mount unit in accordance with one embodiment of the disclosure. Applications of the HGU 501 include home, office, hotel, cool rooms, manufacturing, medical, automotive (car/truck) and marine. The wall/flush-mount unit covers up to 45 square meters, depending on demand.

Figure 15:
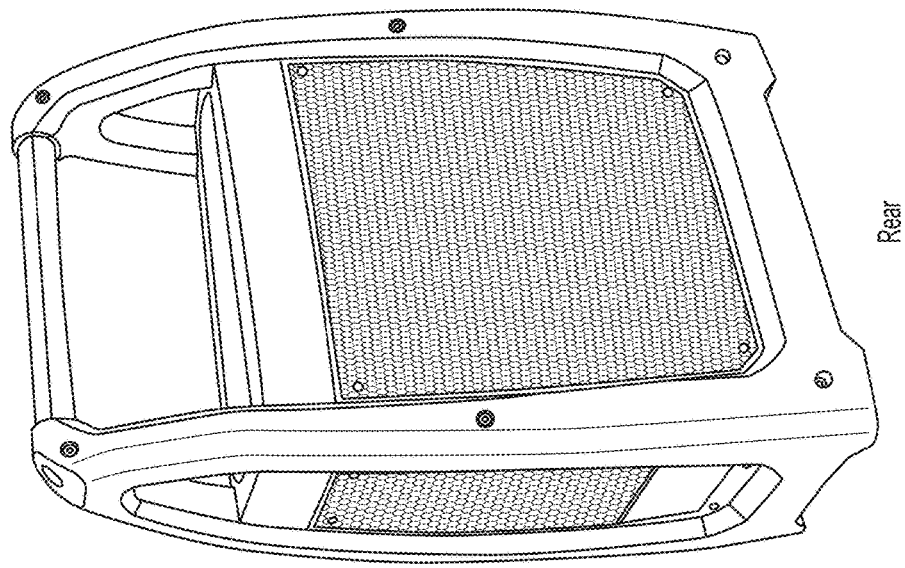
FIGS. 14 and 15 are photographs of a commercial/restoration unit in accordance with one embodiment of the disclosure.
Figure 14:
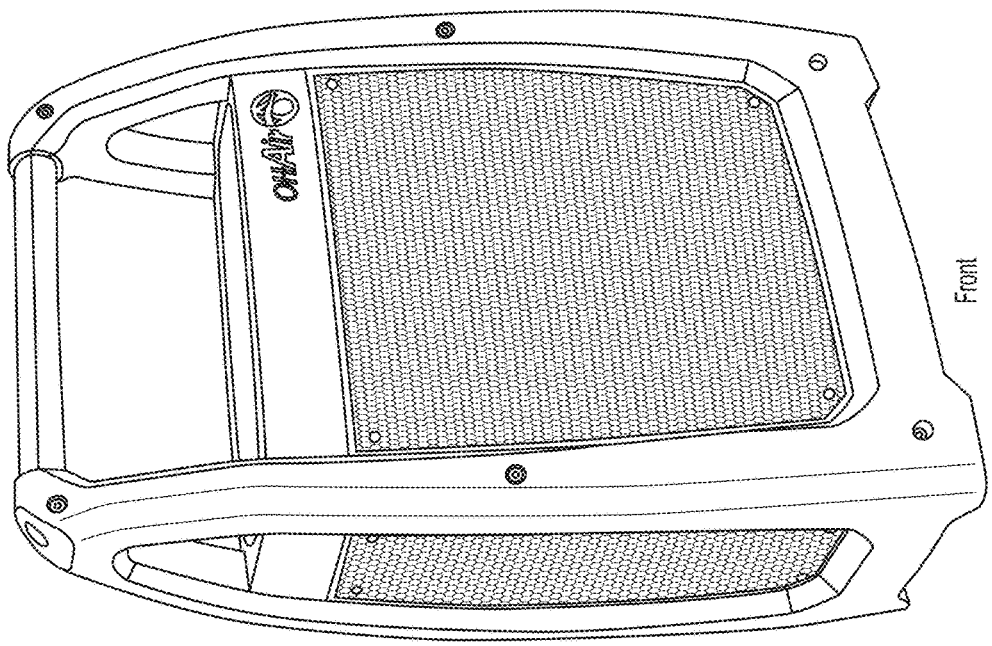

FIGS. 14 and 15 are photographs of a commercial/restoration unit in accordance with one embodiment of the disclosure.

Figure 16:
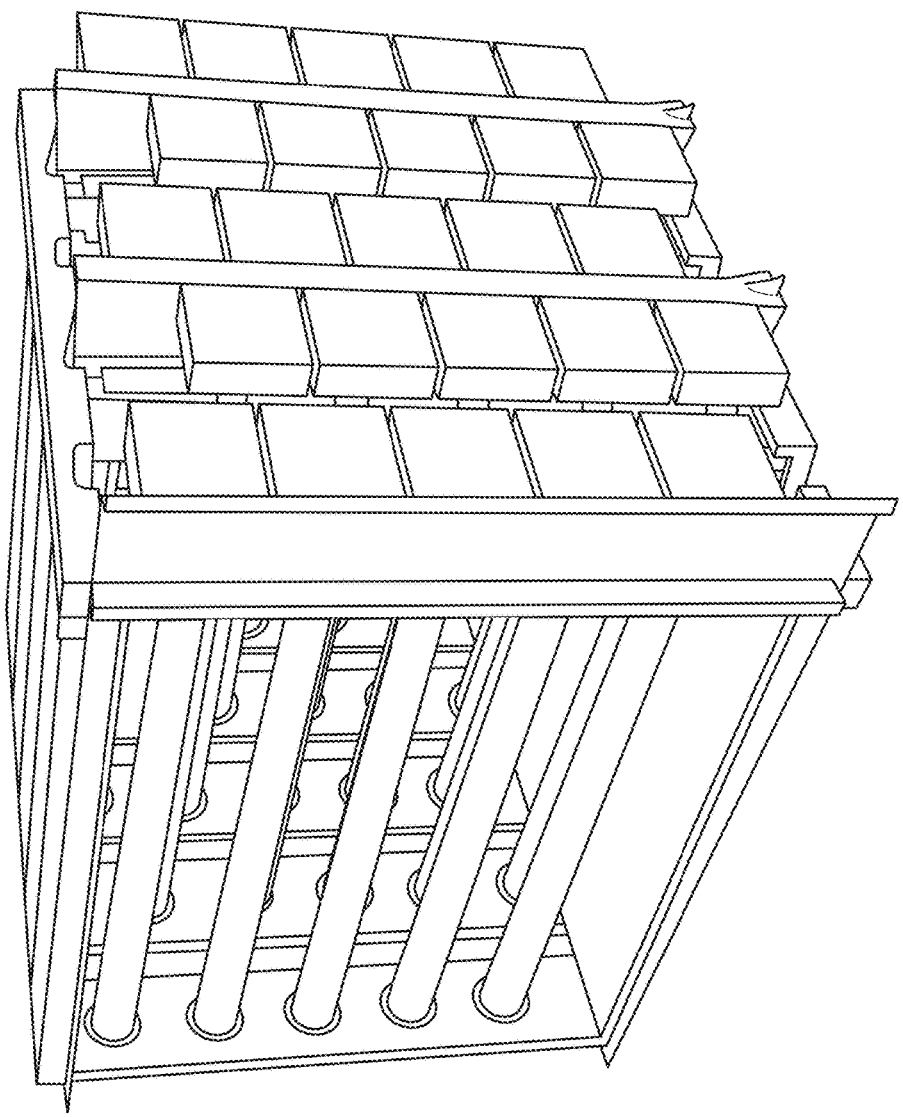
FIG. 16 is a photograph of a fully assembled 5×5 lamp rack in accordance with one embodiment of the disclosure.

FIG. 16 is a photograph of a fully assembled 5×5 lamp rack in accordance with one embodiment of the disclosure. Embodiments include rack units—industrial/commercial.

Figure 18:
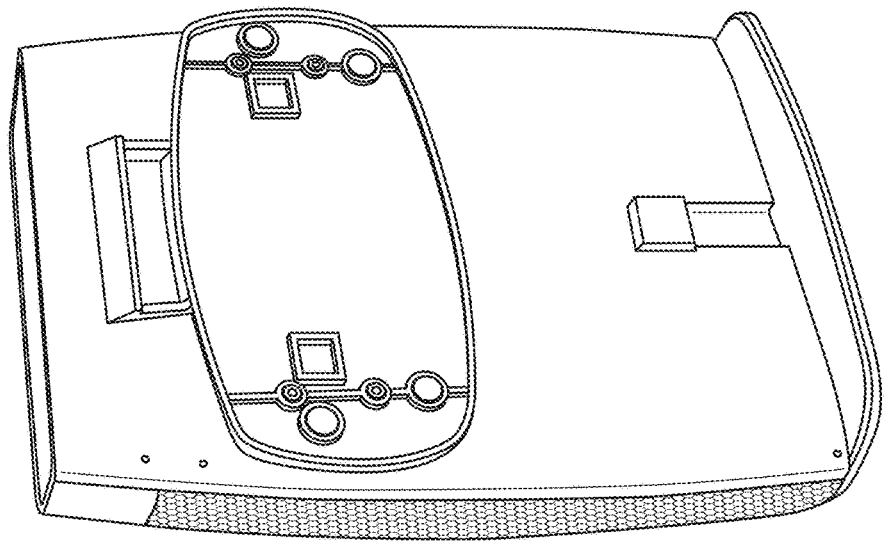
FIGS. 17 and 18 are photographs of a floor/wall unit in accordance with one embodiment of the disclosure.
Figure 17:
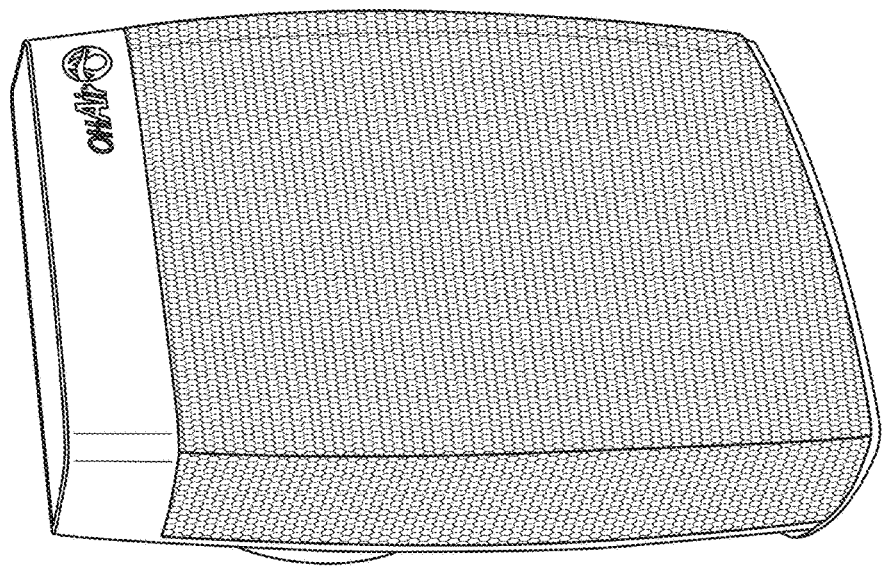

FIGS. 17 and 18 are photographs of a floor/wall unit in accordance with one embodiment of the disclosure.

Figure 20:
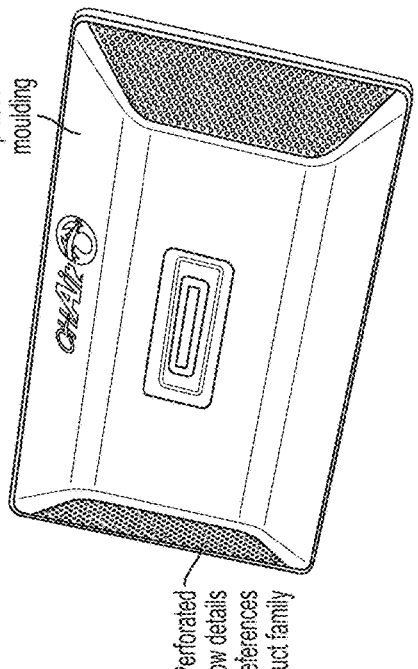
FIGS. 19 and 20 are photographs of a wall mounted sensor/control unit in accordance with one embodiment of the disclosure.
Figure 19:
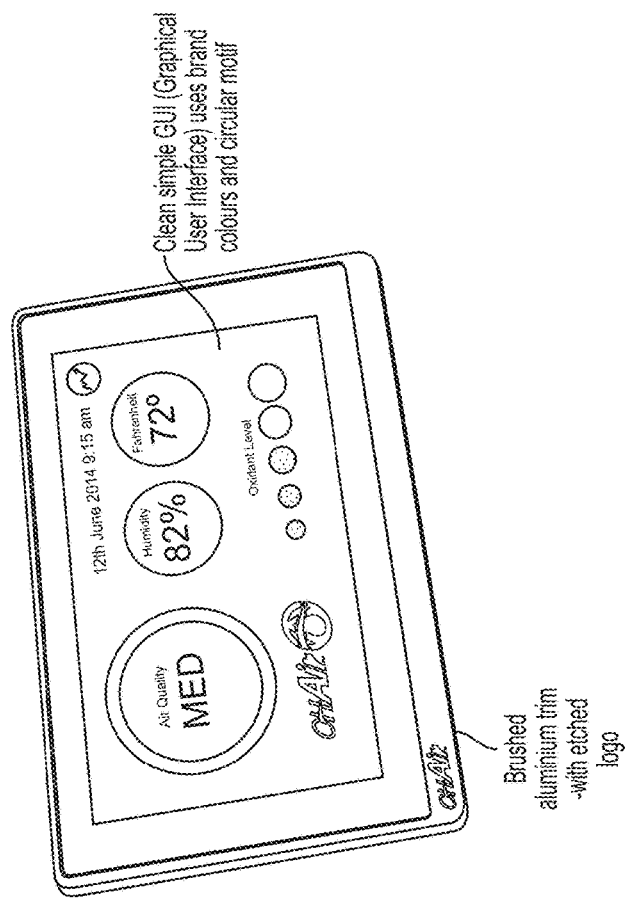
Figure 23:
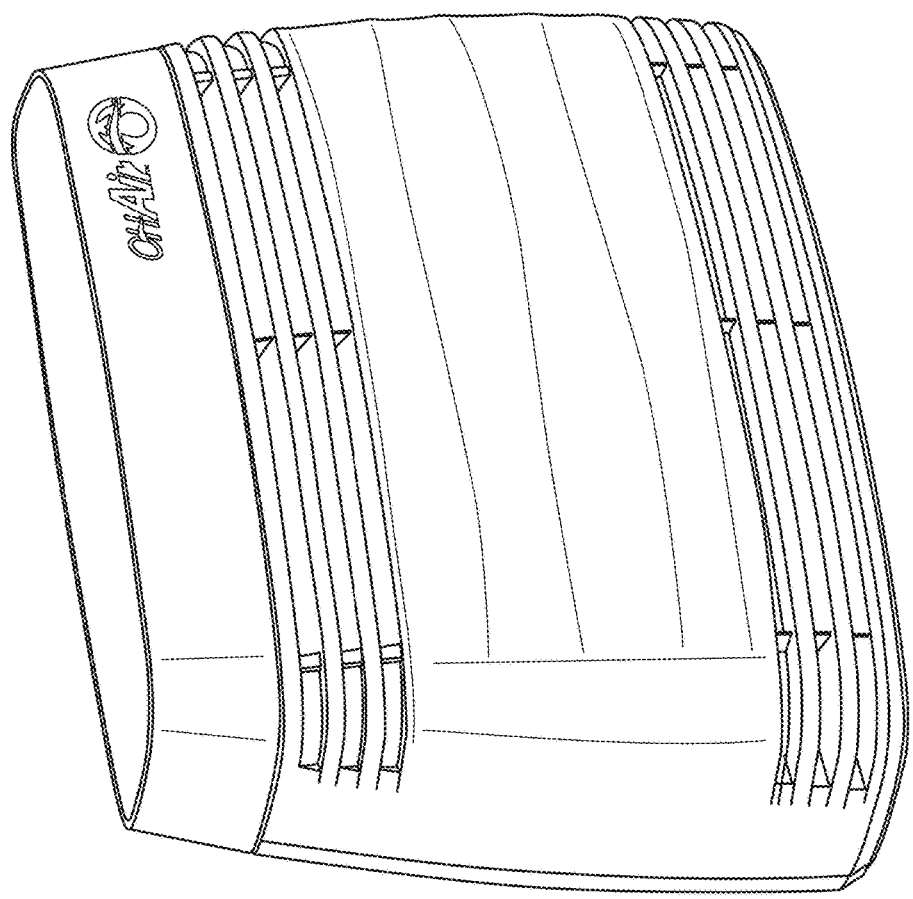
FIG. 23 is a perspective view of the personal unit of FIGS. 7, 8 and 9.

FIGS. 19 and 20 are photographs of a wall mounted sensor/control unit in accordance with one embodiment of the disclosure. In one embodiment, the HGU 501 includes a wall mounted sensor/control unit. The wall mounted sensor/control unit has a clean, simple graphical user interface. The wall mounted sensor/control unit has a circular motif. The wall mounted sensor/control unit has a brushed aluminum trim, and brushed finish plastic molding. The wall mounted sensor/control unit has perforated airflow details.

FIGS. 21 and 22 show test results of the HGU 501 in accordance with one embodiment of the disclosure.

U.S. Pat. No. 9,168,323 B2, issued Oct. 27, 2015 to Guy J. E. Morneault, which is assigned to the assignee of the present patent application, and which describes operation of a hydroxyl generator unit such as the hydroxyl generator unit 501 in more detail, is hereby fully incorporated herein.

What is claimed is:

1. A hydroxyl generator unit, comprising:
   an ultraviolet light source;
   a reaction chamber within interior space of the hydroxyl generator unit, wherein the ultraviolet light source is disposed within the reaction chamber;
   at least one environmental sensor to sense an environmental condition; and
   a smart optic controller coupled to the at least one environmental sensor and to the ultraviolet light source, wherein the smart optic controller integrates environmental conditions sensed by the at least one environmental sensor, and in response to at least one environmental condition, the smart optic controller generates an output signal to the ultraviolet light source to control an amount of hydroxyls generated by the hydroxyl generator unit.

2. The hydroxyl generator unit of claim 1, wherein the smart optic controller is removably coupled to the ultraviolet light source.

3. The hydroxyl generator unit of claim 1, wherein the smart optic controller is user-replaceable.

4. The hydroxyl generator unit of claim 1, wherein the smart optic controller includes one or more of the following environmental sensors: an air flow sensor, a temperature sensor, a humidity sensor and a light sensor.

5. The hydroxyl generator unit of claim 4, wherein the smart optic controller includes a microcontroller that interrogates the environmental sensors and that interfaces to external systems.

6. The hydroxyl generator unit of claim 5, wherein the smart optic controller includes a near field communications circuit attached to a sensor communications link, and a control interface via an RS-485 serial data communications port.

7. The hydroxyl generator unit of claim 6, wherein the smart optic controller includes:
   a SmartUser interface coupled to the microcontroller; and
   a Bluetooth circuit, coupled to the microcontroller.

* * * * *